United States Patent [19]
Goldstein et al.

[11] Patent Number: 5,531,777
[45] Date of Patent: Jul. 2, 1996

[54] HEAT AND COLD PACKS CONTAINING GARNET CRYSTALS

[76] Inventors: Karen L. Goldstein; Kirby L. Mannon, both of 115 4th Ave. W., Kalispell, Mont. 59901

[21] Appl. No.: 380,582

[22] Filed: Jan. 30, 1995

[51] Int. Cl.$^6$ ........................................................ A61F 7/03
[52] U.S. Cl. ..................................................... 607/114
[58] Field of Search ............................... 607/96, 108–114

[56] References Cited

U.S. PATENT DOCUMENTS

| | | | |
|---|---|---|---|
| 3,900,035 | 8/1975 | Welch et al. | 607/108 |
| 3,980,070 | 9/1976 | Krupa | 607/114 X |
| 4,573,447 | 3/1986 | Thrash et al. | 607/114 X |
| 4,865,012 | 9/1989 | Kelley | 607/114 X |
| 5,086,770 | 2/1992 | Prangley | 607/88 |
| 5,391,198 | 2/1995 | Cheney, III et al. | 607/114 |

*Primary Examiner*—Angela D. Sykes
*Attorney, Agent, or Firm*—Richard L. Huff

[57] ABSTRACT

A heat or cold pack composed of a flexible container and a composition comprising crystals which are exited to vibration by heat, moisture-absorbent fiber particles, and temperature-retaining solid particles. The pack is capable of drawing moisture from the air. Heating of the pack causes excitation and vibration of the crystals which then causes penetration of heat or cold into the deep tissues similar to ultra-sound therapy. Sequential application of cooled and heated packs are useful for the treatment of sprains, pulled muscles, edema caused by injuries, and other conditions.

13 Claims, No Drawings

HEAT AND COLD PACKS CONTAINING GARNET CRYSTALS

BACKGROUND OF THE INVENTION

1. Field of the Invention

This invention relates to heat packs and cold packs and methods of using them.

2. Description of the Related Art

The prior art is aware of packs which can serve either as heat packs or cold packs, as see U.S. Pat. Nos. 3,889,684, 4,592,358, and 5,245,938. The prior art is also aware of heat packs which absorb moisture from the atmosphere. Such heat packs are suitable for delivering moist heat to the site of the body on which the heat pack is placed. Other patents pertinent to the field of heat and cold packs are U.S. Pat. Nos. 3,977,202, 4,72,827, 4,756,299 and 5,088,549. None of the heat or cold packs known by the prior art are capable of delivering moist heat or cold to the deep tissues and to effect healing of deep injuries. For purposes of this invention, "deep" is defined as a distance of 3 cm below the surface of the skin.

SUMMARY OF THE INVENTION

It is an object of the present invention to provide compositions for use in heat and cold packs, the heat and cold packs containing these compositions, and methods of treating mammals with these heat and cold packs. The heat and cold packs of the present invention contain crystals which vibrate when heated. When used in heat packs, the preheating of these crystals causes excitation and vibration of the crystals. When used in cold packs, the heating of these crystals caused by body heat causes excitation and vibration of the crystals. This vibration aids in delivering heat or cold to the deep tissues similar to the action of ultra-sound and offering deep heat or cold therapy which is suitable for a wider variety of conditions than is treatable by the prior art packs. Upon being heated, the crystals of the present invention increase their speed of vibration, and upon application to a body, are capable of discharging energy into that body.

Upon cooling, the packs of the present invention absorb moisture. Upon heating, moisture is given off. Surprisingly, the packs of the present invention give off moisture when they are being used as heat or cold packs. Cold packs containing moisture, when applied to a body, absorb heat from the body and give off moisture to the body. When heated packs containing moisture are applied to the body, moisture is given off to the body until the moisture content of the pack is equal to the relative humidity of the surrounding air. The degree of therapy brought about by the heat and cold packs of the present invention is also greater than the degree of therapy brought about by the prior art packs.

DESCRIPTION OF THE PREFERRED EMBODIMENTS

The compositions of the present invention comprise three components.

The first component is a mineral in crystal form which is excited to vibration by the presence of heat. One such crystal is quartz. Garnet crystals, particularly the deep red crystals, are preferred for this invention. The size of the crystals is not critical and may vary over a large range. Preferred are those crystals having a diameter between 0.005 and 0.6 cm. Particularly preferred ranges are between 0.2 and 0.6 cm. The crystals may be used alone for some conditions, particularly arthritis. In such cases, the heated crystals are applied directly to the area of pain, the treated area is wrapped and the crystals are held in place for approximately forty-five minutes. Preferably, the crystals are combined with fibers for moisture absorption and other solid particles as fillers for retention of heat or cold. Thus, the crystals may be present in a proportion of 15 to 100% of the composition. Unless stated otherwise, all proportions are by weight. For use in the heat or cold packs, preferred ranges of the crystals are 15 to 70%.

The second ingredient of the composition is a fiber material which serves to absorb moisture. Preferably, the fibers of natural grain such as rice, buckwheat, and millet are used. Additionally, natural fibers from the leaves and stalks of plants are suitable. The length of the fiber is not critical, however a range of 0.2 to 1.0 cm is preferrred. The proportions of the fibers in the composition are not critical, although a range of 20 to 80% is preferred. A range of 20–70% is more greatly preferred.

The third ingredient is a temperature-retaining filler. Any inert, soild material is suitable for this purpose. Examples of fillers are minerals such as calcium, iron, manganese, sand, and clay. Natural salts such as silicates, are preferred. Ground minerals, such as rocks may be used. The size of the filler is not critical. A preferred diameter is from 0.001 to 1.0 cm. A more preferred range is 0.05–1.0 cm. The proportions of the filler in the composition are not critical, however a range of 4–70% is preferred and a range of 10 to 60% is more preferred.

Optional ingredients such as proteins, niacin, and thiamine may be incorporated in minor amounts.

The composition is prepared by mixing together desired proportions of the ingredients in any sequence.

The heat or cold pack is prepared by placing the composition in a flexible container which will contain the composition while allowing the passage of moisture, and permanently closing the container. Permeable material such as water-permeable plastic or canvas is useful as the container material. The pack may take a variety of forms. Flat packs having dimensions of 25 by 32.5 cm or 24 by 24 cm may be used. Also, packs especially made to fit on the eyes or neck may be used. Such shaped packs are known in the art. The packs may be cooled by freezing in a freezing compartment. The packs may be heated by placing them in a microwave (1–2 minutes at a setting of high) or conventional oven (5–15 minutes at 350° F.). The safe use of hot or cold packs may be ensured by wrapping the packs in towels.

EXAMPLES 1–3

A 24 by 24 cm canvas pack containing 850 gm of a composition made up of 40% red garnet crystals having a diameter of 0.4 cm, 55% of rice fibers having a length of 0.7 cm, and 5% of ground granite having a diameter of 0.1 cm as temperature-maintaining filler was stored in a freezer. the thus-produced cold pack was covered by terry cloth and applied to a sprained ankle over a period of 48–72 hours. Following this treatment, the same pack was heated in a microwave for 2 minutes on a setting of high, covered with terry cloth, and applied to the ankle. The same pack, cooled and heated in the same manner, was applied to pulled muscles and edematous sores using the same regimen as described above. In all cases, the swelling and pain disappeared.

EXAMPLE 4

A heated canvas 24 by 24 cm pack containing 800 gm of a composition containing 20% red garnet having a diameter of about 0.4 cm, 75% rice fiber having a length of 0.7 cm as a moisture absorbent agent, and 5% of clay having a diameter of 0.05 cm as a heat-retaining filler was applied to the abdomen, hips, and lower back for the successful relief of menstrual cramps.

EXAMPLE 5

A heated canvas pack having a size of 24 by 24 cm containing 900 gm of a composition made up of 60% red garnet having a diameter of about 0.5 cm, 35% of millet fibers having a length of about 0.2 cm, 4% of sand having a diameter of 0.1 cm as a temperature-retaining filler, and 0.5% each of thiamine and niacin was applied to the forehead of a patient suffering from a headache. Simultaneously, a cooled canvas pack shaped to fit the neck, and containing a composition as just described was applied to the back of the neck. The headache was successfully alleviated.

EXAMPLE 6

Patients having fever were successfully treated to reduce the fever by applying cooled packs containing the composition described in Example 5 to the temporal area, the axilla, the forehead, and the back of the neck.

EXAMPLE 7

Patients suffering from systemic lupus applied heated canvas 24 by 24 cm packs containing the composition of Example 5 to areas of the pain. The pain was greatly reduced, and in some cases, actually disappeared.

EXAMPLE 8

Patients exhibiting pain caused by sinus infections applied heated canvas packs shaped to fit over the eyes and containing the composition of Example 5. After a period of 5 to 15 minutes, the pain was substantially gone.

In similar fashion, heated packs containing compositions of the present invention may be applied to the neck and shoulders to relieve stress.

Pain from gout may be relieved by applying cold packs of this invention simultaneously to the top and bottom of the feet.

Pain from whiplash injuries may be alleviated by applying cooled cervical packs containing compositions according to this invention to the neck over a period of 48 to 72 hours to control swelling followed by application of heated packs to increase the blood supply.

Insomnia may be treated by the application of heated larger size packs according to this invention to various areas of the body Colic may be treated by applying a slightly warmed pack according to this invention to the feet of the baby, then laying the child on a slightly heated pack for approximately 5 minutes.

Relief of rheumatoid arthritis pain and increased mobility of the affected joints may be obtained by applying heated garnet crystals to the affected areas, wrapping the treated areas, and maintaining application for approximately 45 minutes.

Temporal-mandibular joint pain may be relieved by applying heated packs according to this invention to the temporal and jaw areas.

It will be noticed that the user does not have to add water to the packs of the present invention, thus the packs are not messy and are easy to work with. Beneficial moisture is provided as the fibers of the composition absorb moisture from the air, which moisture can then be released to the body.

The packs of the present invention should not be used on any single area for more than 15 to 20 minutes per hour. Also, injury due to excessive heat may be avoided by placing terry cloth between the skin and the pack.

We claim:

1. A composition for heat and cold packs comprising crystalline minerals which vibrate without decomposing when excited by heat to a temperature of 350° F., moisture-absorbing fibers, and temperature-retention solid particles.

2. A composition for heat and cold packs as claimed in claim 1, wherein the crystalline materials are garnet crystals, the absorbent fibers are plant fibers originating in a portion of the plant selected from the group consisting of grain, leaf and stalk, and the granules of temperature-retaining solids are selected from the group consisting of sand, clay, and granite.

3. The composition of claim 2, wherein the garnet crystals are present in a range of 15 to 70% of the composition, the moisture-absorbent fibers are present in a range of 20 to 80% of the composition, and the solid temperature-retaining granules are present in a range of 4 to 70% of the composition.

4. The composition of claim 3, wherein the garnet crystals have a diameter between 0.2 and 0.6 cm, the moisture-absorbent fibers have a length between 0.2 and 1.0 cm, and the temperature-retaining particles have a diameter between 0.05 and 1.0 cm.

5. A heat or cold pack comprising a flexible container containing a composition comprising the composition of claim 4.

6. A heat or cold pack comprising a flexible container conatining a composition comprising the composition of claim 3.

7. A heat or cold pack comprising a flexible container containing a composition comprising the composition of claim 2.

8. A heat or cold pack comprising a flexible container containing a composition comprising the composition of claim 1.

9. The heat or cold pack of claim 8, wherein the flexible container is made of canvas.

10. A method of treating mammalian bodies for conditions requiring topical cold therapy, which comprises cooling the pack of claim 5 and applying said pack to a portion of the body requiring cold therapy.

11. A method of treating mammalian bodies for conditions requiring topical heat therapy, which comprises heating the pack of claim 5 and applying said pack to a portion of the body requiring heat therapy.

12. A method of treating an injury in a mammalian body, which comprises cooling the pack of claim 8 to prepare a cold pack, applying the cold pack to the site of the injury for 15 to 20 minutes at a time over a period of 48 to 72 hours with recooling of the pack when needed, then heating the pack of claim 8 to prepare a heat pack, and applying the heat pack to the injury for a time sufficient to produce vasodilation and hyperemia with reheating of the pack when needed.

13. A method of treating joint pain from rheumatoid arthritis, which comprises applying heated red garnet crystals to the painful joints, wrapping the joints to which the garnet has been applied and maintaining contact for approximately 45 minutes.

* * * * *